United States Patent
Tanaka et al.

(10) Patent No.: US 7,423,180 B2
(45) Date of Patent: Sep. 9, 2008

(54) BIS(3-AMINO-4-HYDROXYPHENYL) ADAMANTANE DERIVATIVES AND PROCESS FOR PRODUCTION THEREOF

(75) Inventors: Shinji Tanaka, Chiba (JP); Hidetoshi Ono, Chiba (JP); Kouichi Kodoi, Chiba (JP); Naoyoshi Hatakeyama, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 214 days.

(21) Appl. No.: 10/547,553

(22) PCT Filed: Feb. 26, 2004

(86) PCT No.: PCT/JP2004/002280

§ 371 (c)(1), (2), (4) Date: Sep. 1, 2005

(87) PCT Pub. No.: WO2004/078701

PCT Pub. Date: Sep. 16, 2004

(65) Prior Publication Data

US 2006/0161016 A1 Jul. 20, 2006

(30) Foreign Application Priority Data

Mar. 4, 2003 (JP) ............................ 2003-056780

(51) Int. Cl.
*C07C 211/00* (2006.01)
(52) U.S. Cl. .................................................. 564/315
(58) Field of Classification Search .................. None
See application file for complete search history.

(56) References Cited

FOREIGN PATENT DOCUMENTS

| FR | 2 399 454 | 3/1979 |
|---|---|---|
| JP | 40-21771 | 9/1965 |
| JP | 5-271105 | 10/1993 |
| JP | 11-106365 | 4/1999 |
| JP | 2002-173470 | 6/2002 |
| JP | 2002-265422 | 9/2002 |
| JP | 2004-18593 | 1/2004 |

OTHER PUBLICATIONS (Chemical Abstract 1979:524216; abstract of FR 2399454).*
Despax, B. et al.: "Radiostability of Polybenzoxazoles. Comparison of Stability of Molecular Ions of Model Compounds in Mass Spectrometry with Resistance of the Polymers to Ionizing Radiations", Journal of Applied Polymer Science, vol. 27, No. 1, pp. 225-234, Jan. 1982.

Despax, B. et al.: "Comparative Study of the Photodegration of Polybenzoxzoles and Related Model Compounds. Stabilization of Polybenzoxazoles", Journal of Polymer Science, vol. 18, No. 2, pp. 593-609, Feb. 1980.
Munoz, A. et al., "Spirophosphoranes Macromoleculaires", European Polymer Journal, vol. 15, No. 7, pp. 631-638, Feb. 5, 1979.

* cited by examiner

*Primary Examiner*—Samuel A Barts
(74) *Attorney, Agent, or Firm*—Oblon, Spivak, McClelland, Maier & Neustadt, P.C.

(57) ABSTRACT

The invention provides compounds which are excellent in terms of heat resistance, mechanical characteristics, electric characteristics, physical properties, etc. and which provide a novel material useful for, for example, interlayer insulating film or protective film for use in semiconductor devices, interlayer insulating film for use in multilayer wiring boards, cover coating in flexible printed circuits, or a liquid crystal alignment layer.

The compounds are bis(3-amino-4-hydroxyphenyl)adamantane derivatives having a structure represented by formula (I) or (II):

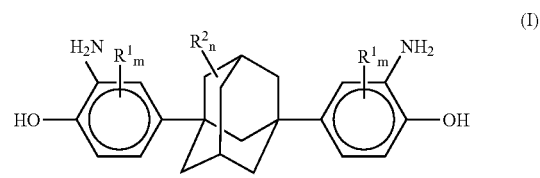

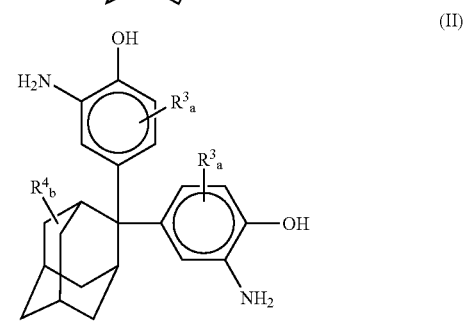

(each of $R^1$ to $R^4$ represents a halogen atom, a hydroxyl group, an alkyl group, an alkoxyl group, a carboxyl group, or an alkoxycarbonyl group, each of m and a is an integer of 0 to 3, and each of n and b is an integer of 0 to 14, with the proviso that the case where the following three conditions in formula (I) are met is excluded: $R^2$ is methyl and present at a bridgehead; m is 0; and n is 2).

4 Claims, No Drawings

BIS(3-AMINO-4-HYDROXYPHENYL) ADAMANTANE DERIVATIVES AND PROCESS FOR PRODUCTION THEREOF

TECHNICAL FIELD

The present invention relates to novel bis(3-amino-4-hydroxy)adamantane derivatives and to a process for producing the same. More particularly, the invention relates to novel bis(3-amino-4-hydroxy)adamantane derivatives which are excellent in terms of heat resistance, mechanical characteristics, electric characteristics, physical properties, etc. and which may be used as a starting material for producing polybenzoxazole that is useful for, for example, interlayer insulating film or protective film for use in semiconductor devices, interlayer insulating film for use in multilayer wiring boards, cover coating of flexible printed circuits, or a liquid crystal alignment layer, and to a process for producing the same at high efficiency.

BACKGROUND ART

A bis(o-aminophenol) compound is reacted with an aromatic dicarboxylic acid or an acid component containing an amide-formable derivative, thereby forming a polybenzoxazole. Polybenzoxazole is known to form an interlayer insulating film or surface-protective film for use in multi-layer wiring boards, etc. (see, for example, Japanese Patent Application Laid-Open (kokai) Nos. 2002-275264 and 5-102125).

Meanwhile, adamantane is a highly symmetric, stable compound by virtue of the structure thereof in which four cyclohexane rings are fused to form a cage-like skeleton. Adamantane exhibits low dielectric constant, which is characteristic to alicyclic compounds, and adamantane derivatives exhibit various functions. Therefore, adamantane and derivatives thereof are known to be useful sources for producing drugs, high-performance industrial materials, etc. Specifically, studies have been performed on production of optical elements such as optical disk substrates, optical fiber, and lenses from these compounds having optical characteristics and heat resistance (see, for example, Japanese Patent Application Laid-Open (kokai) Nos. 6-305044 and 9-302077). Application to photoresist resin sources of adamantane esters having acid-sensitivity, dry etching resistance, UV transparency, and other properties has been studied (see, for example, Japanese Patent Application Laid-Open (kokai) No. 4-39665).

In the meantime, in the field of semiconductor devices, lead-free solder and copper wiring have been employed in order to keep pace with the trend for micro-scaling of the devices. During packaging steps (e.g., encapsulation with resin, lead frame bonding, and wire bonding), LSI chips must be protected from heat and mechanical shock (e.g., 300° C. and 30 MPa). As a result, heat resistance of semiconductor devices per se has been of increasing importance in the production of the devices.

Furthermore, in the field of LSIs, there have been carried out micro-wiring for realizing high-speed operation and elevating integration degree through increase in the number of layers stacked. This raises the problem of signal delay called RC delay. Thus, interlayer insulating film or other elements are required to have lower dielectric constant.

DISCLOSURE OF THE INVENTION

The present invention has been made under such circumstances, and an object of the present invention is to provide a compound which is excellent in terms of heat resistance, mechanical characteristics, electric characteristics, physical properties, etc. and which provides a novel material useful for, for example, interlayer insulating film or protective film for use in semiconductor devices, interlayer insulating film for use in multilayer wiring boards, cover coating in flexible printed circuits, or a liquid crystal alignment layer.

The present inventors have carried out extensive studies on the compound capable of providing a novel material useful in the aforementioned applications, paying special attention to the adamantane skeleton, and have found that a certain class of bis(3-amino-4-hydroxyphenyl)adamantane derivatives having a specified structure, which are novel compounds and have never been disclosed in literature, can readily form polybenzoxazole, which is suitable for the aforementioned applications. The present invention has been accomplished on the basis of this finding.

Accordingly, (1) the present invention provides a 1,3-bis(3-amino-4-hydroxyphenyl)adamantane derivative characterized by having a structure represented by formula (I):

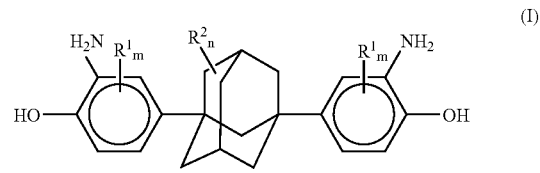

(wherein each of $R^1$ and $R^2$ represents a halogen atom, a hydroxyl group, a C1-C10 alkyl group, a C1-C10 alkoxyl group, a carboxyl group, or an alkoxycarbonyl group having a C1-C10 alkyl group; m is an integer of 0 to 3; n is an integer of 0 to 14; when m is 2 or more, a plurality of $R^1$s may be identical to or different from one another; and when n is 2 or more, a plurality of $R^2$s may be identical to or different from one another; with the proviso that the case where the following three conditions are met is excluded: $R^2$ is methyl and present at a bridgehead; m is 0; and n is 2). Hereinafter, the derivative is referred to as "adamantane derivative I of the present invention."

(2) The present invention also provides a 2,2-bis(3-amino-4-hydroxyphenyl)adamantane derivative characterized by having a structure represented by formula (II):

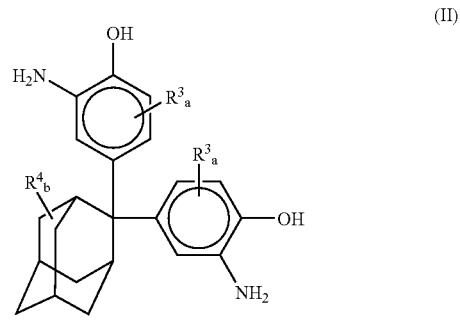

(wherein each of $R^3$ and $R^4$ represents a halogen atom, a hydroxyl group, a C1-C10 alkyl group, a C1-C10 alkoxyl group, a carboxyl group, or an alkoxycarbonyl group having a C1-C10 alkyl group; a is an integer of 0 to 3; b is an integer of 0 to 14; when a is 2 or more, a plurality of $R^3$s may be identical to or different from one another; and when b is 2 or more, a plurality of $R^4$s may be identical to or different from one another) Hereinafter, the derivative is referred to as "adamantane derivative II of the present invention."

(3) The present invention also provides a process for producing a 1,3-bis(3-amino-4-hydroxyphenyl)adamantane derivative represented by formula (I):

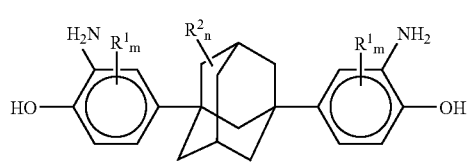

(I)

(wherein $R^1$, $R^2$, m, and n have the same meanings as defined above, with the proviso that the case where the following three conditions are met is excluded: $R^2$ is methyl and present at a bridgehead; m is 0; and n is 2), characterized in that the process comprises performing nitration of a 1,3-bis(4-hydroxyphenyl)adamantane derivative represented by formula (III):

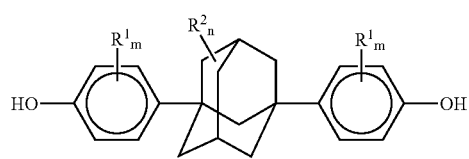

(III)

(wherein $R^1$, $R^2$, m, and n have the same meanings as defined above, with the proviso that the case where the following three conditions are met is excluded: $R^2$ is methyl and present at a bridgehead; m is 0; and n is 2), and reducing the nitration product.

(4) The present invention also provides a process for producing a 2,2-bis(3-amino-4-hydroxyphenyl)adamantane derivative represented by formula (II):

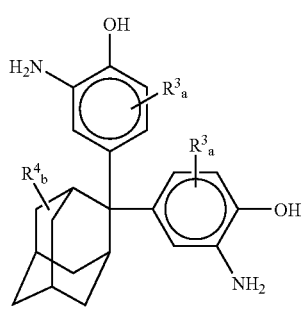

(II)

(wherein $R^3$, $R^4$, a, and b have the same meanings as defined above), characterized in that the process comprises performing nitration of a 2,2-bis(4-hydroxyphenyl)adamantane derivative represented by formula (IV):

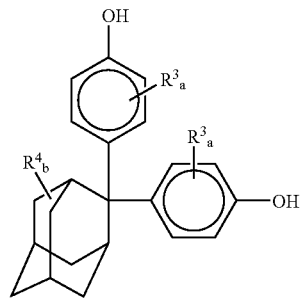

(IV)

(wherein $R^3$, $R^4$, a, and b have the same meanings as defined above), and reducing the nitration product.

BEST MODES FOR CARRYING OUT THE INVENTION

The bis(3-amino-4-hydroxyphenyl)adamantane derivative of the present invention includes two modes; adamantane derivative I and adamantane derivative II.

The adamantane derivative I of the present invention is a 1,3-bis(3-amino-4-hydroxyphenyl)adamantane derivative, which is a novel compound and has never been disclosed in literature, having a structure represented by (I).

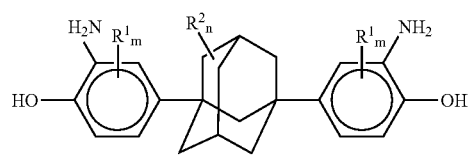

(I)

In formula (I), each of $R^1$ and $R^2$ represents a halogen atom, a hydroxyl group, a C1-C10 alkyl group, a C1-C10 alkoxyl group, a carboxyl group, or an alkoxycarbonyl group having a C1-C10 alkyl group. Examples of the halogen atom includes fluorine, chlorine, bromine, and iodine. The C1-C10 alkyl group may be linear, branched, or cyclic, and may have an appropriate substituent such as a halogen atom. Examples of such alkyl groups include methyl, ethyl, n-propyl, isopropyl, butyl groups, pentyl groups, hexyl groups, octyl groups, decyl groups, cyclopentyl, cyclohexyl, trifluoromethyl, and perfluoroethyl.

The alkyl groups in the C1-C10 alkyl groups and in the alkoxycarbonyl groups having a C1-C10 alkyl group are the same as described above.

In formula (I), m is an integer of 0 to 3; n is an integer of 0 to 14; when m is 2 or more, a plurality of $R^1$s may be identical to or different from one another; and when n is 2 or more, a plurality of $R^2$s may be identical to or different from one another; with the proviso that the case where the following three conditions are met is excluded: $R^2$ is methyl and present at a bridgehead; m is 0; and n is 2.

The adamantane derivative II of the present invention is a 2,2-bis(3-amino-4-hydroxyphenyl)adamantane derivative, which is a novel compound and has never been disclosed in literature, having a structure represented by (II).

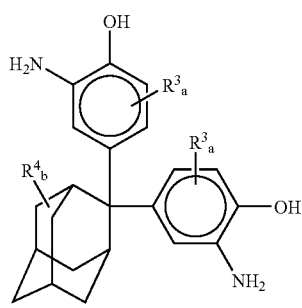

(II)

In formula (II), each of $R^3$ and $R^4$ represents a halogen atom, a hydroxyl group, a C1-C10 alkyl group, a C1-C10 alkoxyl group, a carboxyl group, or an alkoxycarbonyl group having a C1-C10 alkyl group. $R^3$ and $R^4$ are the same as described in relation to $R^1$ and $R^2$ in formula (I).

In formula (II), a is an integer of 0 to 3; b is an integer of 0 to 14; when a is 2 or more, a plurality of $R^3$s may be identical to or different from one another; and when b is 2 or more, a plurality of $R^4$s may be identical to or different from one another.

Examples of 1,3-bis(3-amino-4-hydroxyphenyl)adamantane derivatives represented by formula (I) include 1,3-bis(3-amino-4-hydroxyphenyl)adamantane, 1,3-bis(3-amino-4-hydroxy-5-methylphenyl)adamantane, 1,3-bis(3-amino-4-hydroxy-5-ethylphenyl)adamantane, 1,3-bis(3-amino-4-hydroxy-5-methoxyphenyl)adamantane, 1,3-bis(3-amino-4-hydroxy-5-ethoxyphenyl)adamantane, 1,3-bis(3-amino-4-hydroxy-5-fluorophenyl)adamantane, 1,3-bis(3-amino-4-hydroxy-5-trifluoromethylphenyl)adamantane, 1,3-bis(3-amino-4-hydroxy-5-perfluoroethylphenyl)adamantane, 1,3-bis(3-amino-4-hydroxy-5-trifluoromethoxyphenyl)adamantane, 1,3-bis(3-amino-4-hydroxy-5-perfluoroethoxyphenyl)adamantane, 1,3-bis(3-amino-4-hydroxy-2,5-difluorophenyl)adamantane, 1,3-bis(3-amino-2,4-dihydroxyphenyl)adamantane, 1,3-bis(3-amino-2,4,6-trihydroxyphenyl)adamantane, 1,3-bis(3-amino-4-hydroxyphenyl)-5-methyladamantane, 1,3-bis(3-amino-4-hydroxyphenyl)-5,7-diethyladamantane, 1,3-bis(3-amino-4-hydroxyphenyl)-5-fluoroadamantane, 1,3-bis(3-amino-4-hydroxyphenyl)-5,7-difluoroadamantane, 1,3-bis(3-amino-4-hydroxyphenyl)-5-trifluoromethyladamantane, 1,3-bis(3-amino-4-hydroxyphenyl)-5,7-bis(trifluoromethyl)adamantane, and 1,3-bis(3-amino-4-hydroxyphenyl)perfluoroadamantane.

Examples of 2,2-bis(3-amino-4-hydroxyphenyl)adamantane derivatives represented by formula (II) include 2,2-bis(3-amino-4-hydroxyphenyl)adamantane, 2,2-bis(3-amino-4-hydroxy-5-methylphenyl)adamantane, 2,2-bis(3-amino-4-hydroxy-5-ethylphenyl)adamantane, 2,2-bis(3-amino-4-hydroxy-5-methoxyphenyl)adamantane, 2,2-bis(3-amino-4-hydroxy-5-ethoxyphenyl)adamantane, 2,2-bis(3-amino-4-hydroxy-5-fluorophenyl)adamantane, 2,2-bis(3-amino-4-hydroxy-5-trifluoromethylphenyl)adamantane, 2,2-bis(3-amino-4-hydroxy-5-perfluoroethylphenyl)adamantane, 2,2-bis(3-amino-4-hydroxy-5-trifluoromethoxyphenyl)adamantane, 2,2-bis(3-amino-4-hydroxy-5-perfluoroethoxyphenyl)adamantane, 2,2-bis(3-amino-4-hydroxy-2,5-difluorophenyl)adamantane, 2,2-bis(3-amino-2,4-dihydroxyphenyl)adamantane, 2,2-bis(3-amino-2,4,6-trihydroxyphenyl)adamantane, 2,2-bis(3-amino-4-hydroxyphenyl)-5-methyladamantane, 2,2-bis(3-amino-4-hydroxyphenyl)-5,7-diethyladamantane, 2,2-bis(3-amino-4-hydroxyphenyl)-5-fluoroadamantane, 2,2-bis(3-amino-4-hydroxyphenyl)-5,7-difluoroadamantane, 2,2-bis(3-amino-4-hydroxyphenyl)-5-trifluoromethyladamantane, 2,2-bis(3-amino-4-hydroxyphenyl)-5,7-bis(trifluoromethyl)adamantane, and 2,2-bis(3-amino-4-hydroxyphenyl)perfluoroadamantane.

The adamantane derivatives I and II of the present invention may be produced through, for example, the following procedure.

According to the process of the present invention, 1,3-bis(3-amino-4-hydroxyphenyl)adamantane derivatives represented by formula (I), which are adamantane derivatives I of the present invention, may be produced by performing nitration of a 1,3-bis(4-hydroxyphenyl)adamantane derivative represented by formula (III):

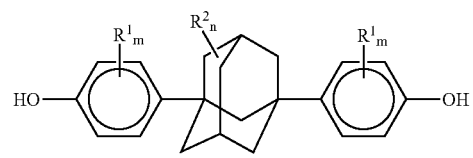

(III)

(wherein $R^1$, $R^2$, m, and n have the same meanings as defined above, with the proviso that the case where the following three conditions are met is excluded: $R^2$ is methyl and present at a bridgehead; m is 0; and n is 2), and reducing the nitration product.

2,2-Bis(3-amino-4-hydroxyphenyl)adamantane derivatives represented by formula (II), which are adamantane derivatives II of the present invention, may be produced by performing nitration of a 2,2-bis(4-hydroxyphenyl)adamantane derivative represented by formula (IV):

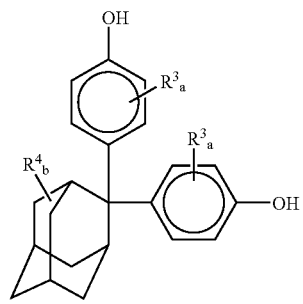

(IV)

(wherein $R^3$, $R^4$, a, and b have the same meanings as defined above), and reducing the nitration product.

In the above process, nitration is generally performed by use of an agent for nitration such as nitric acid in a solvent, for example, a dehydrating solvent such as acetic anhydride or propionic anhydride and, in accordance with needs, at least one optional solvent selected from among ether solvents such as diethyl ether, tetrahydrofuran, and dioxane; aliphatic hydrocarbon solvents such as hexane, heptane, and octane; and aromatic hydrocarbon solvents such as benzene, toluene, and xylene. The optional solvent has been dehydrated in advance through a routine method. The reaction conditions are as follows: reaction temperature: generally −78 to 100°

C., preferably 0° C. to room temperature; reaction pressure: generally 0.1 to 10 MPa, preferably ambient pressure; and reaction time: generally 1 to 24 hours, preferably 2 to 6 hours. No particular limitation is imposed on the concentration of starting material, and a concentration equal to or lower than the solubility (saturated). Generally, a concentration of about 0.1 to 1.0 mol/L is appropriate.

As described above, a 1,3-bis(4-hydroxy-3-nitrophenyl) adamantane derivative is produced from a 1,3-bis(4-hydroxyphenyl)adamantane derivative represented by formula (III), and a 2,2-bis(4-hydroxy-3-nitrophenyl)adamantane derivative is produced from a 2,2-bis(4-hydroxyphenyl)adamantane derivative represented by (IV).

No particular limitation is imposed on the reduction of the thus-obtained nitration product, and any of known methods may be employed. In the present invention, preferably, the nitration product is added to an appropriate solvent and reduced by use of a reducing agent such as hydrogen gas in the presence of a reduction catalyst.

Examples of the solvent employed in the reduction include alcohol solvents such as methanol, ethanol, propanol, and butanol; ether solvents such as diethyl ether, tetrahydrofuran, and dioxane; aliphatic hydrocarbon solvents such as hexane, heptane, and octane; and aromatic hydrocarbon solvents such as benzene, toluene, and xylene. These solvents may be used singly or in combination of two or more species. Examples of the reduction catalyst include palladium/carbon (Pd/C) and metal (nickel, platinum, etc.)-on-carrier (alumina, silica, zeolite, ZSM-5, MCM-41, etc.). Generally, hydrogen gas is employed as a reducing agent.

The reduction conditions are as follows: reaction temperature: generally −78 to 100° C., preferably 0° C. to room temperature; reaction pressure: generally 0.1 to 10 MPa, preferably ambient pressure; and reaction time: generally 1 to 48 hours, preferably 10 to 30 hours. No particular limitation is imposed on the concentration of starting material, and a concentration equal to or lower than the solubility (saturated). Generally, a concentration of about 0.1 to 1.0 mol/L is appropriate.

Through the reduction, nitro groups are converted to amino groups, whereby adamantane derivatives I and II of the present invention can be produced.

Meanwhile, 1,3-bis(4-hydroxyphenyl)adamantane derivatives and 2,2-bis(4-hydroxyphenyl)adamantane derivatives, serving as starting materials, may be produced through a known method.

The bis(3-amino-4-hydroxyphenyl)adamantane derivative of the present invention is reacted with, for example, a dicarboxylic acid, to thereby form a polybenzoxazole according to the following reaction scheme (A):

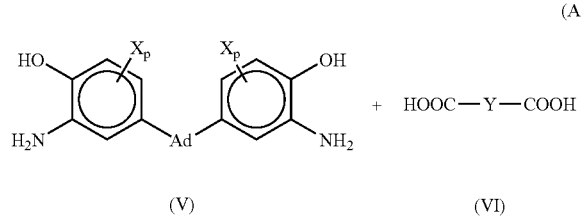

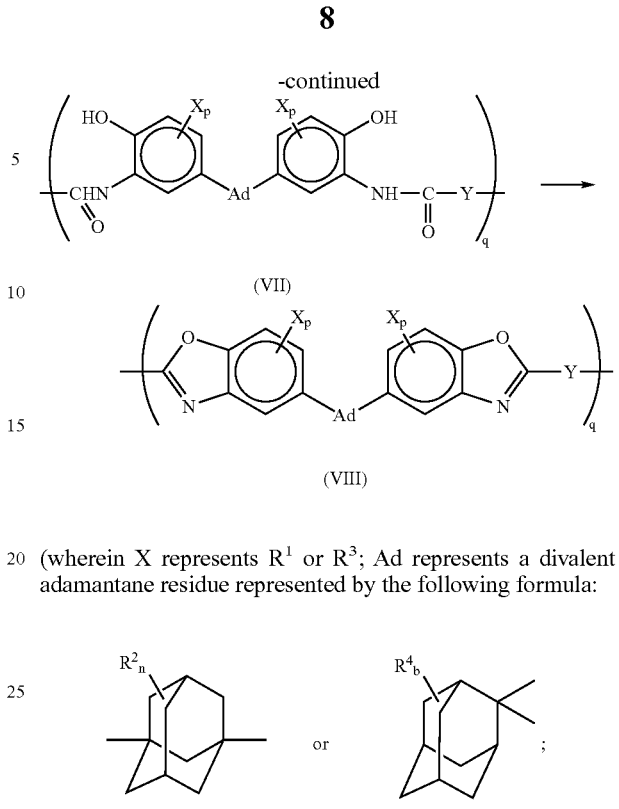

(wherein X represents $R^1$ or $R^3$; Ad represents a divalent adamantane residue represented by the following formula:

Y represents a dicarboxylic acid residue; p is m or a; q represents a polymerization degree; and $R^1$, $R^2$, $R^3$, $R^4$, m, n, a, and b have the same meanings as defined above).

As shown in reaction scheme (A), the bis(3-amino-4-hydroxyphenyl)adamantane derivative (V) of the present invention is reacted with a dicarboxylic acid (VI), to thereby form a polyhydroxyamide (VII). Through subsequent heating, a polybenzoxazole (VIII) is formed.

The aforementioned dicarboxylic acid (VI) may be aliphatic, alicyclic, or aromatic. Examples of the aliphatic dicarboxylic acid include oxalic acid, malonic acid, succinic acid, adipic acid, and pimelic acid. Examples of the alicyclic dicarboxylic acid include 1,2-cyclopentanedicarboxylic acid, and 1,2-, 1,3-, and 1,4-cyclohexanedicarboxylic acids. Examples of the aromatic dicarboxylic acid include isophthalic acid, 4-fluoroisophthalic acid, 4-chloroisophthalic acid, 4-methylisophthalic acid, 2,4,5,6-tetrafluoroisophthalic acid, 5-fluoroisophthalic acid, 5-trifluoromethylisophthalic acid, 5-trifluoromethoxyisophthalic acid, terephthalic acid, 2-fluoroterephthalic acid, 2-chloroterephthalic acid, 2-methylterephthalic acid, 2,3,5,6-tetrafluoroterephthalic acid, 2,2-bis(4-carboxyphenyl)propane, 2,2-bis(4-carboxyphenyl)hexafluoropropane, 4,4'-phenyldicarboxylic acid, 2,2'-bis(trifluoromethyl)-4,4'-biphenyldicarboxylic acid, 4,4'-diphenyl ether dicarboxylic acid, 3,3'-diphenyl ether dicarboxylic acid, 4,4'-benzophenonedicarboxylic acid, bis(4-carboxyphenyl) sulfone, bis(4-carboxyphenyl) sulfide, bis(4-carboxyphenyl)tetraphenyldisiloxane, and 2,6-naphthalenedicarboxylic acid.

An amide-formable derivative may also employed as the aforementioned dicarboxylic acid. Examples of the amide-formable derivative include dicarboxylic acid dihalides and active esters between dicarboxylic acid and hydroxybenzotriazole.

In the case where film of the polybenzoxazole (VIII) is formed, generally, a varnish prepared by dissolving a polyhydroxyamide (VII) serving as a precursor in a solvent is applied to form a coating film, followed by heating, whereby polybenzoxazole (VIII) film is formed.

The thus-formed polybenzoxazole film is excellent in heat resistance, mechanical characteristics, electric characteristics, physical properties, etc., and is useful for, for example, interlayer insulating film or protective film for use in semiconductor devices, interlayer insulating film for use in multilayer wiring boards, cover coating in flexible printed circuits, or liquid crystal alignment layer.

In addition to the above applications, the bis(3-amino-4-hydroxyphenyl)adamantane derivative of the present invention may be used as optical materials including optical fiber, optical waveguide, and optical disks. The derivative of the present invention may also be a candidate for an drug intermediate, a coating additive (e.g., heat resistance enhancer), a resin additive (e.g., heat resistance enhancer), etc.

EXAMPLES

The present invention will next be described in detail by way of examples, which should not be construed as limiting the invention thereto.

Example 1

(1) Synthesis of 1,3-bis(4-hydroxy-3-nitrophenyl)adamantane

To a 10-L four-neck flask, 1,3-bis(4-hydroxyphenyl)adamantane (180 g, 562 mmol) and acetic anhydride (4,500 mL) were fed. The formed slurry was stirred on an ice bath. Subsequently, 60 mass % nitric acid (142 g, 1,349 mmol) was added to the slurry over 1.5 hours, while the temperature inside the flask was maintained at 10° C. or lower. The slurry was gradually dissolved, to form a yellow-brown solution. Thereafter, yellow solid is precipitated from the solution.

Subsequently, the reaction mixture was fed to ice water (3,000 mL), and the mixture was subjected to filtration with suction and washing with methanol. The thus-obtained solid was dried under reduced pressure, to thereby yield 162 g (394 mmol) of 1,3-bis(4-hydroxy-3-nitrophenyl)adamantane as yellow powder (yield: 70%).

(2) Synthesis of 1,3-bis(3-amino-4-hydroxyphenyl)adamantane

To a 3-L two-neck flask, 1,3-bis(4-hydroxy-3-nitrophenyl)adamantane obtained in (1) above (161 g, 392 mmol), ethanol (1,610 mL), and 10 mass % Pd/C (8.05 g) were fed, to thereby form a slurry. After the inside of the reactor had been purged with hydrogen, the slurry was stirred at room temperature for 21 hours. During stirring, the slurry was changed from yellow to white as reaction proceeded. N,N-dimethylformamide (1,000 mL) was added to the reaction mixture, followed by heating at 50° C. for dissolution. The mixture was filtrated by use of Celite.

The filtrate was concentrated under reduced pressure, and methanol/diethyl ether solution (ratio by mass: 20/80) (1,000 mL) was added to the obtained residue. The mixture was stirred at room temperature for 30 minutes, whereby the solid was washed. The mixture was subjected to filtration with suction, followed by washing with diethyl ether (200 mL). Methanol/diethyl ether solution (ratio by mass: 20/80) (200 mL) was added to the solid, followed by stirring at room temperature for 30 minutes. The mixture was subjected to filtration with suction, and the solid was washed with methanol/diethyl ether solution (ratio by mass: 10/90) (100 mL). The thus-obtained solid was dried under reduced pressure (0.7 kPa, 50° C., 1 hour), to thereby yield 63.1 g (180 mmol) of the target 1,3-bis(3-amino-4-hydroxyphenyl)adamantane as pale gray powder (yield: 46%).

Physical properties of the compound is as follows.
Nuclear magnetic resonance (NMR):DMSO-$d_6$
$^1$H-NMR(500 MHz): 1.69 to 2.18(m,14H,a-e), 4.36 (br-s, 4H, NH$_2$), 6.40(dd,J=2.1 Hz, 8.2 Hz, 2H,g or h or k), 6.56(d, J=8.2 Hz,2H,g or h or k), 6.65(d,J=2.1 Hz,2H,g or h or k), 8.70(br-s,2H,OH)
$^{13}$C-NMR(126 MHz): 29.21(c), 35.65(e), 36.07(a), 42.36 (b), 49.53(d), 111.50(g or h or k), 112.55(g or h or k), 113.94(g or h or k), 135.78(j), 141.89(f and i)

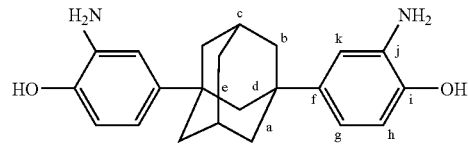

Example 2

(1) Synthesis of 2,2-bis(4-hydroxy-3-nitrophenyl)adamantane

To a 2-L four-neck flask, 2,2-bis(4-hydroxyphenyl)adamantane (180 g, 562 mmol) and acetic anhydride (900 mL) were fed. The formed slurry was stirred on an ice bath. Subsequently, 60 mass % nitric acid (142 g, 1,349 mmol) was added to the slurry over 2 hours, while the temperature inside the flask was maintained at 10° C. or lower. The slurry was gradually dissolved, to form a yellow-brown solution.

Subsequently, the reaction mixture was fed to ice water (900 mL), and the formed organic layer is separated and concentrated, to thereby yield 273 g of a crude product. Methanol (900 mL) was added to the crude product, to thereby form a suspension. The suspension was refluxed for 20 minutes, followed by washing and cooling to 40° C. The mixture was subjected to filtration with suction and washing with methanol (500 mL). The thus-obtained solid was dried under reduced pressure, to thereby yield 191 g (465 mmol) of 2,2-bis(4-hydroxy-3-nitrophenyl)adamantane as yellow powder (yield: 83%).

Physical properties of the compound is as follows.
Nuclear magnetic resonance (NMR):CDCl$_3$
$^1$H-NMR(500 MHz): 1.73~1.95(m,12H,i-k), 3.19(s,2H, b), 7.07(d,J=9.0 Hz, 2H,b), 7.61(d,J=2.3 Hz,J=9.0 Hz,2H,c), 8.08(d,J=2.3 Hz,2H,e)
$^{13}$C-NMR(126 MHz): 27.20(h or j), 31.93(j or h), 32.88(i or k), 37.55(k or i), 49.45(g), 120.61(b or c or e), 121.89(b or c or e), 133.71(a or d or f), 135.28(b or c or e), 140.16(a or d or f), 152.82 (a or d or f)

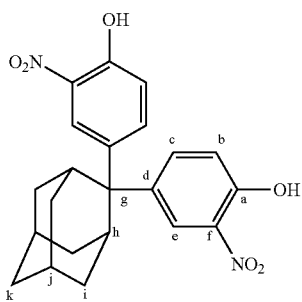

(2) Synthesis of 2,2-bis(3-amino-4-hydroxyphenyl)adamantane

To a 3-L two-neck flask, 2,2-bis(4-hydroxy-3-nitrophenyl)adamantane obtained in (1) above (190 g, 463 mmol), ethanol (1,900 mL), and 10 mass % Pd/C (9.80 g) were fed, to thereby form a slurry. After the inside of the reactor had been purged with hydrogen, the slurry was stirred at room temperature for 30 hours. During stirring, the slurry was changed from yellow to colorless as reaction proceeded. N,N-dimethylformamide (300 mL) was added to the reaction mixture, for dissolution. The mixture was filtrated by use of Celite.

The filtrate was concentrated under reduced pressure, and diethyl ether (700 mL) was added to the obtained residue. The mixture was stirred at room temperature for 30 minutes, followed by filtration with suction. The thus-obtained solid was dried under reduced pressure (0.7 kPa, 50° C., 4 hours), to thereby yield 163 g (463 mmol) of the target 2,2-bis(3-amino-4-hydroxyphenyl)adamantane as pale brown powder (yield: 100%).

Physical properties of the compound is as follows.

Nuclear magnetic resonance (NMR):CDCl$_3$/DMSO-d$_6$ $^1$H-NMR(500 MHz): 1.63 to 2.05(m,12H, i-k), 3.00(s,2H, h), 3.87(br-s,4H,NH$_2$), 6.51 to 6.55(m,4H,b or c or e), 6.67 (s,2H,b or c or e), 8.35(br-s,2H,OH)

$^{13}$C-NMR(126 MHz): 26.17(h or j), 30.54(j or h), 32.21(i or k),36.82 (k or i), 47.75(g), 111.83(b or c or e), 113.45(b or c or e), 113.99(b or c or e), 133.77(a or d or f), 139.52 (a or d or f), 140.11(a or d or f)

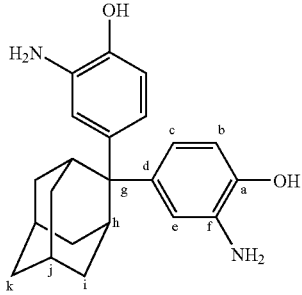

INDUSTRIAL APPLICABILITY

The present invention can provide a novel bis(3-amino-4-hydroxyphenyl)adamantane derivative which is excellent in terms of heat resistance, mechanical characteristics, electric characteristics, physical properties, etc. and which provides a source for polybenzoxazole useful for, for example, interlayer insulating film or protective film for use in semiconductor devices, interlayer insulating film for use in multilayer wiring boards, cover coating in flexible printed circuits, or a liquid crystal alignment layer.

The invention claimed is:

1. A 1,3-bis(3-amino-4-hydroxyphenyl)adamantane derivative according to formula (I):

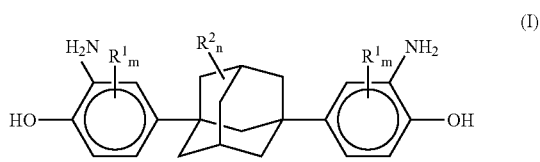

wherein R$^1$ and R$^2$ each independently represent a halogen atom, a hydroxyl group, a C1-C10 alkyl group, a C1-C10 alkoxyl group, a carboxyl group, or an alkoxycarbonyl group having a C1-C10 alkyl group; m is an integer of 0 to 3; n is an integer of 0 to 14; when m is 2 or more, a plurality of R$^1$s may be identical to or different from one another; and when n is 2 or more, a plurality of R$^2$s may be identical to or different from one another; with the proviso that the case where the following three conditions are met is excluded: R$^2$ is methyl and present at a bridgehead; m is 0; and n is 2.

2. A 2,2-bis(3-amino-4-hydroxyphenyl)adamantane derivative according to formula (II):

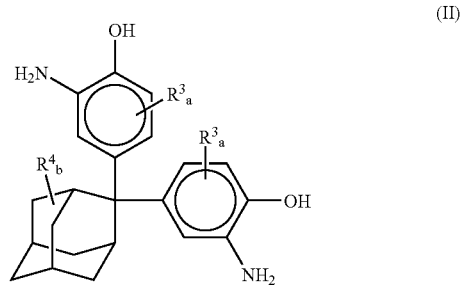

wherein R$^3$ and R$^4$ each independently represent a halogen atom, a hydroxyl group, a C1-C10 alkyl group, a C1-C10 alkoxyl group, a carboxyl group, or an alkoxycarbonyl group having a C1-C10 alkyl group; a is an integer of 0 to 3; b is an integer of 0 to 14; when a is 2 or more, a plurality of R$^3$s may be identical to or different from one another; and when b is 2 or more, a plurality of R$^4$s may be identical to or different from one another; with the proviso that the case where the following three conditions are met is excluded: R$^4$ is methyl and present at a bridgehead; a is 0; and b is 2.

3. A process for producing a 1,3-bis(3-amino-4-hydroxyphenyl)adamantane derivative according to formula (I):

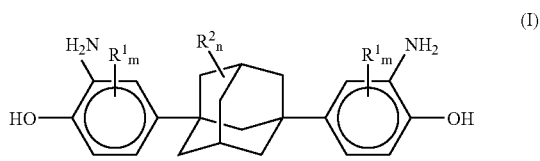

wherein $R^1$ and $R^2$ each independently represent a halogen atom, a hydroxyl group, a C1-C10 alkyl group, a C1-C10 alkoxyl group, a carboxyl group, or an alkoxycarbonyl group having a C1-C10 alkyl group; m is an integer of 0 to 3; n is an integer of 0 to 14; when m is 2 or more, a plurality of $R^1$s may be identical to or different from one another; and when n is 2 or more, a plurality of $R^2$s may be identical to or different from one another; with the proviso that the case where the following three conditions are met is excluded: $R^2$ is methyl and present at a bridgehead; m is 0; and n is 2, wherein the process comprises:

performing nitration of a 1,3-bis(4-hydroxyphenyl)adamantane derivative according to formula (III):

(III)

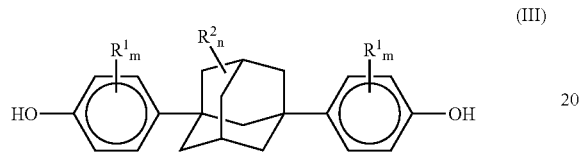

to produce a nitration product, wherein $R^1$, $R^2$, m, and n have the same meanings as defined above, with the proviso that the case where the following three conditions are met is excluded: $R^2$ is methyl and present at a bridgehead; m is 0; and n is 2; and reducing the nitration product to produce the 1,3-bis(3-amino-4-hydroxyphenyl)adamantane derivative according to formula (I).

4. A process for producing a 2,2-bis(3-amino-4-hydroxyphenyl)adamantane derivative according to formula (II):

(II)

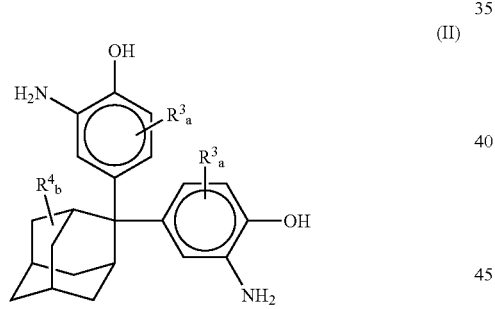

wherein $R^3$ and $R^4$ each independently represent a halogen atom, a hydroxyl group, a C1-C10 alkyl group, a C1-C10 alkoxyl group, a carboxyl group, or an alkoxycarbonyl group having a C1-C10 alkyl group; a is an integer of 0 to 3; b is an integer of 0 to 14; when a is 2 or more, a plurality of $R^3$s may be identical to or different from one another; and when b is 2 or more, a plurality of $R^4$s may be identical to or different from one another; with the proviso that the case where the following three conditions are met is excluded: $R^4$ is methyl and present at a bridgehead; a is 0; and b is 2, wherein the process comprises:

performing nitration of a 2,2-bis(4-hydroxyphenyl)adamantane derivative according to formula (IV):

(IV)

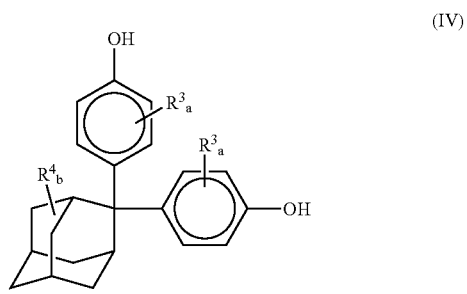

to produce a nitration product, wherein $R^3$, $R^4$, a, and b have the same meanings as defined above, with the proviso that the case where the following three conditions are met is excluded: $R^4$ is methyl and present at a bridgehead; a is 0; and b is 2; and reducing the nitration product to produce the 2,2-bis(3-amino-4-hydroxyphenyl)adamantane derivative according to formula (II).

* * * * *